United States Patent [19]
Jackson et al.

[11] Patent Number: 5,925,539
[45] Date of Patent: Jul. 20, 1999

[54] HUMAN PELOTA HOMOLOG

[75] Inventors: Jeffrey Richard Jackson, Collegeville, Pa.; Michael Joseph Hansbury, Collingswood, N.J.

[73] Assignee: SmithKline Beecham Corporation, Philadelphia, Pa.

[21] Appl. No.: 09/145,947

[22] Filed: Sep. 2, 1998

Related U.S. Application Data

[62] Division of application No. 08/892,715, Jul. 15, 1997.

[51] Int. Cl.$^6$ .............................. C12P 21/06; C12Q 1/68
[52] U.S. Cl. ................................. 435/68.1; 435/6
[58] Field of Search .............................. 435/68.1, 6, 69.1

[56] References Cited

PUBLICATIONS

EST 68772.

Primary Examiner—Eggerton A. Campbell
Attorney, Agent, or Firm—William T. Han; Ratner & Prestia; William T. King

[57] ABSTRACT

68772 polypeptides and polynucleotides and methods for producing such polypeptides by recombinant techniques are disclosed. Also disclosed are methods for utilizing 68772 polypeptides and polynucleotides in the design of protocols for the treatment of proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, among others, and diagnostic assays for such conditions.

2 Claims, No Drawings

5,925,539

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1632 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

| | |
|---|---|
| CCCGGGCGCT GCAGTGTTCC CCGAGCCTGT TAGACGCAGC GCGCCGGGAG ACTGAGAGAG | 60 |
| GAAAGGATAG AGGAAGTGCT GCCCTAGGCT GCATGAGTCG AAGCAAGCGT GTTTCCTTCC | 120 |
| CGCCAGGCAA GTGCCCTTAG AAACCGGGCC CCGCCCCCTT CCTGGCCTGC ATTCCCATCC | 180 |
| CCTCTCCCGG GGCGGAGGTG AGGACCTCCT TGGTTCCTTT GGTTCTGTCA GTGAGCCCCT | 240 |
| TCCTTGGCCA TGAAGCTCGT GAGGAAGAAC ATCGAGAAGG ACAATGCGGG CCAGGTGACC | 300 |
| CTGGTCCCCG AGGAGCCTGA GGACATGTGG CACACTTACA ACCTCGTGCA GGTGGGCGAC | 360 |
| AGCCTGCGCG CCTCCACCAT CCGCAAGGTA CAGACAGAGT CCTCCACGGG CAGCGTGGGC | 420 |
| AGCAACCGGG TCCGCACTAC CCTCACTCTC TGCGTGGAGG CCATCGACTT CGACTCTCAA | 480 |
| GCCTGCCAGC TGCGGGTTAA GGGGACCAAC ATCCAAGAGA ATGAGTATGT CAAGATGGGG | 540 |
| GCTTACCACA CCATCGAGCT GGAGCCCAAC CGCCAGTTCA CCCTGGCCAA GAAGCAGTGG | 600 |
| GATAGTGTGG TACTGGAGCG CATCGAGCAG GCCTGTGACC CAGCCTGGAG CGCTGATGTG | 660 |
| GCGGCTGTGG TCATGCAGGA AGGCCTCGCC CATATCTGCT TAGTCACTCC CAGCATGACC | 720 |
| CTCACTCGGG CCAAGGTGGA GGTGAACATC CCTAGGAAAA GGAAAGGCAA TTGCTCTCAG | 780 |
| CATGACCGGG CCTTGGAGCG GTTCTATGAA CAGGTGGTCC AGGCTATCCA GCGCCACATA | 840 |
| CACTTTGATG TTGTAAAGTG CATCCTGGTG GCCAGCCCAG GATTTGTGAG GGAGCAGTTC | 900 |
| TGCGACTACA TGTTTCAACA AGCAGTGAAG ACCGACAACA AACTGCTCCT GGAAAACCGG | 960 |
| TCCAAATTTC TTCAGGTACA TGCCTCCTCC GGACACAAGT ACTCCCTGAA AGAGGCCCTT | 1020 |
| TGTGACCCTA CTGTGGCTAG CCGCCTTTCA GACACTAAAG CTGCTGGGGA AGTCAAAGCC | 1080 |
| TTGGATGACT TCTATAAAAT GTTACAGCAT GAACCGGATC GAGCTTTCTA TGGACTCAAG | 1140 |
| CAGGTGGAGA AGGCCAATGA AGCCATGGCA ATTGACACAT TGCTCATCAG CGATGAGCTC | 1200 |
| TTCAGGCATC AGGATGTAGC CACACGGAGC CGGTATGTGA GGCTGGTGGA CAGTGTGAAA | 1260 |
| GAGAATGCAG GCACCGCTAG GATATTCTCT AGTCTTCACG TTTCTGGGGA ACAGCTCAGC | 1320 |
| CAGTTGACTG GGGTAGCTGC CATTCTCCGC TTCCCTGTTC CCGAACTTTC TGACCAAGAG | 1380 |
| GGTGATTCCA GTTCTGAAGA GGATTAATGA TTGAAACTTA AAATTGAGAC AATCTTGTGT | 1440 |
| TTCCTAAACT GTTACAGTAC ATTTCTCAGC ATCCTTGTGA CAGAAAGCTG CAAGAAGGGC | 1500 |
| ACTTTTTGAT TCATACAGGG ATTTCTTATG TCTTTGGCTA CACTAGATAT TTTGTGATTG | 1560 |
| GCAAGACATG TATTTAAACA ATAAACTAAA AGGAAATAAT CTCCACGTAC TACCAAAAAA | 1620 |
| AAAAAAAAA AA | 1632 |

(2) INFORMATION FOR SEQ ID NO:2:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Leu Val Arg Lys Asn Ile Glu Lys Asp Asn Ala Gly Gln Val
 1               5                  10                  15

Thr Leu Val Pro Glu Glu Pro Glu Asp Met Trp His Thr Tyr Asn Leu
                20                  25                  30

Val Gln Val Gly Asp Ser Leu Arg Ala Ser Thr Ile Arg Lys Val Gln
            35                  40                  45

Thr Glu Ser Ser Thr Gly Ser Val Gly Ser Asn Arg Val Arg Thr Thr
```

-continued

```
          50                      55                      60
Leu Thr Leu Cys Val Glu Ala Ile Asp Phe Asp Ser Gln Ala Cys Gln
65                      70                      75                      80

Leu Arg Val Lys Gly Thr Asn Ile Gln Glu Asn Glu Tyr Val Lys Met
                85                      90                      95

Gly Ala Tyr His Thr Ile Glu Leu Glu Pro Asn Arg Gln Phe Thr Leu
                100                     105                     110

Ala Lys Lys Gln Trp Asp Ser Val Val Leu Glu Arg Ile Glu Gln Ala
            115                     120                     125

Cys Asp Pro Ala Trp Ser Ala Asp Val Ala Ala Val Val Met Gln Glu
        130                     135                     140

Gly Leu Ala His Ile Cys Leu Val Thr Pro Ser Met Thr Leu Thr Arg
145                     150                     155                     160

Ala Lys Val Glu Val Asn Ile Pro Arg Lys Arg Lys Gly Asn Cys Ser
                165                     170                     175

Gln His Asp Arg Ala Leu Glu Arg Phe Tyr Glu Gln Val Val Gln Ala
                180                     185                     190

Ile Gln Arg His Ile His Phe Asp Val Val Lys Cys Ile Leu Val Ala
            195                     200                     205

Ser Pro Gly Phe Val Arg Glu Gln Phe Cys Asp Tyr Met Phe Gln Gln
    210                     215                     220

Ala Val Lys Thr Asp Asn Lys Leu Leu Leu Glu Asn Arg Ser Lys Phe
225                     230                     235                     240

Leu Gln Val His Ala Ser Ser Gly His Lys Tyr Ser Leu Lys Glu Ala
                245                     250                     255

Leu Cys Asp Pro Thr Val Ala Ser Arg Leu Ser Asp Thr Lys Ala Ala
                260                     265                     270

Gly Glu Val Lys Ala Leu Asp Asp Phe Tyr Lys Met Leu Gln His Glu
            275                     280                     285

Pro Asp Arg Ala Phe Tyr Gly Leu Lys Gln Val Glu Lys Ala Asn Glu
        290                     295                     300

Ala Met Ala Ile Asp Thr Leu Leu Ile Ser Asp Glu Leu Phe Arg His
305                     310                     315                     320

Gln Asp Val Ala Thr Arg Ser Arg Tyr Val Arg Leu Val Asp Ser Val
                325                     330                     335

Lys Glu Asn Ala Gly Thr Ala Arg Ile Phe Ser Ser Leu His Val Ser
                340                     345                     350

Gly Glu Gln Leu Ser Gln Leu Thr Gly Val Ala Ala Ile Leu Arg Phe
            355                     360                     365

Pro Val Pro Glu Leu Ser Asp Gln Glu Gly Asp Ser Ser Ser Glu Glu
        370                     375                     380

Asp
385
```

HUMAN PELOTA HOMOLOG

This application is a division of application Ser. No. 08/892,715, filed Jul. 15, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Pelota family, hereinafter referred to as 68772. The invention also relates to inhibiting or activating the action of such polynucleotides and polypeptides.

BACKGROUND OF THE INVENTION

Regulation of the cell cycle is controlled by a family of cyclins, cyclin dependent kinases (CDKs), CDK regulatory kinases, and phosphatases. See, Lees, E., Curr. Opin. Cell. Biol. 1995, 7:773–780; Piwinica-Worms, H., J. Lab. Clin. Med. 1996, 128:350–354. Progression from the G2 phase to the M phase of the cell cycle requires the activityof cdc25 phosphatase. In Drosophila, mutations in the pelota gene have the same phenotype as mutations in the twine and/or string genes, which are cdc25 homologs, Eberhart, C. G. and Wasserman. S. A., Devel. 1995, 121:3477–3486. Specific cell cycle effects of pelota mutations are seen in both meiosis and mitosis, including G2/M arrest between mitotic and meiotic cell division, and disruption of nuclear envelope breakdown and spindle formation. Regulation of pelota offers a means of controlling a critical event in the cell cycle.

This indicates that the Pelota family has an established, proven history as therapeutic targets. Clearly there is a need for identification and characterization of further members of Pelota family which can play a role in preventing, ameliorating or correcting dysfunctions or diseases, including, but not limited to, proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas.

SUMMARY OF THE INVENTION

In one aspect, the invention relates to 68772 polypeptides and recombinant materials and methods for their production. Another aspect of the invention relates to methods for using such 68772 polypeptides and polynucleotides. Such uses include the treatment of proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, among others. In still another aspect, the invention relates to methods to identify agonists and antagonists using the materials provided by the invention, and treating conditions associated with 68772 imbalance with the identified compounds. Yet another aspect of the invention relates to diagnostic assays for detecting diseases associated with inappropriate 68772 activity or levels.

DESCRIPTION OF THE INVENTION

Definitions

The following definitions are provided to facilitate understanding of certain terms used frequently herein.

"68772" refers, among others, generally to a polypeptide having the amino acid sequence set forth in SEQ ID NO:2 or an allelic variant thereof.

"68772 activity or 68772 polypeptide activity" or "biological activity of the 68772 or 68772 polypeptide" refers to the metabolic or physiologic function of said 68772 including similar activities or improved activities or these activities with decreased undesirable side-effects. Also included are antigenic and immunogenic activities of said 68772.

"68772 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to 68772 polypeptides (or 68772 proteins). The 68772 polypeptides include the polypeptide of SEQ ID NO:2; as well as polypeptides comprising the amino acid sequence of SEQ ID NO: 2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within 68772 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably 68772 polypeptide exhibit at least one biological activity of 68772.

The 68772 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the 68772 polypeptides are also included in the invention. A fragment is a polypeptide having an amino acid sequence that entirely is the same as part, but not all, of the amino acid sequence of the aforementioned 68772 polypeptides. As with 68772 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of 68772 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of 68772 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate 68772 activity, including those with a similar activity or an improved activity, or with a decreased undesirable activity. Also included are those that are antigenic or immunogenic in an animal, especially in a human.

Preferably, all of these polypeptide fragments retain the biological activity of the 68772, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The 68772 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to 68772 polynucleotides. 68772 polynucleotides include isolated polynucleotides which encode the 68772 polypeptides and fragments, and polynucleotides closely related thereto. More specifically, 68772 polynucleotide of the invention include a polynucleotide comprising the nucleotide sequence set forth in SEQ ID NO:1 encoding a 68772 polypeptide of SEQ ID NO: 2, and polynucleotide having the particular sequence of SEQ ID NO:1. 68772 polynucleotides further include a polynucleotide comprising a nucleotide sequence that has at least 80% identity over its entire length to a nucleotide sequence encoding the 68772 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under 68772 polynucleotides are a nucleotide sequence which has sufficient identity to a nucleotide sequence contained in SEQ ID NO:1 or contained in the cDNA insert in the plasmid deposited with the ATCC Deposit number ATCC 98438 to hybridize under conditions useable for amplification or for use as a probe or marker. Moreover, 68772 polynucleotide include a nucleotide sequence having at least 80% identity to a nucleotide sequence encoding the 68772 polypeptide expressed by the cDNA insert deposited at the ATCC with Deposit Number ATCC 98438, and a nucleotide sequence comprising at least 15 contiguous nucleotides of such cDNA insert. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. The invention also provides polynucleotides which are complementary to all the above 68772 polynucleotides.

A deposit containing a human 68772 cDNA has been deposited with the American Type Culture Collection (ATCC), 12301 Park Lawn Drive, Rockville, Md. 20852, USA, on May 28, 1997, and assigned ATCC Deposit Number ATCC 98438. The deposited material (clone) is SOLR containing UniZap (Stratagene, La Jolla, Calif.) that further contains the full length 68772 cDNA, referred to as "Human pelota cDNA clone from a human T-cell library, ATG-1030" upon deposit. The cDNA insert is within Eco RI, Xho I site(s) in the vector. The nucleotide sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

68772 of the invention is structurally related to other proteins of the Pelota family, as shown by the results of sequencing the cDNA of Table 1 (SEQ ID NO:1) encoding human 68772. The cDNA sequence of SEQ ID NO:1 contains an open reading frame (nucleotide number 250 to 1407) encoding a polypeptide of 385 amino acids of SEQ ID NO:2. Amino acid sequence of Table 2 (SEQ ID NO:2) has about 65% identity (using Gap in GCG (Needleman Wunsch)) in 395 amino acid residues with Drosophila melanogaster pelota (Eberhart and Wasserman, Devel. 121:3477–3486, 1995). Furthermore, 68772 (SEQ ID NO:2) is 36% identical to Saccharomyces cerevisiae DOM34 over 387 amino acid residues (Lalo et al., Compets Rendus de l'Academie des Sciences 316:367–373, 1993). Nucleotide sequence of Table 1 (SEQ ID NO:1) has about 63% identity (using Gap in GCG (Needleman Wunsch)) in 1186 nucleotide residues with Drosophila melanogaster pelota (Eberhart and Wasserman, Devel. 121:3477–3486, 1995). Furthermore, 68772 (SEQ ID NO:1) is 45% identical to Saccharomyces cerevisiae DOM34 over 1176 nucleotide base residues (Lalo et al., Compets Rendus de l'Academie des Sciences 316:367–373, 1993) Thus 68772 polypeptides and polynucleotides of the present invention are expected to have, inter alia, similar biological functions/properties to their homologous polypeptides and polynucleotides, and their utility is obvious to anyone skilled in the art.

TABLE 1[a]

```
CCCGGGCGCTGCAGTGTTCCCCGAGCCTGTTAGACGCAGCGCGCCGGGAGACTGAGAGAGGAAAGGATA
GAGGAAGTGCTGCCCTAGGCTGCATGAGTCGAAGCAAGCGTGTTTCCTTCCCGCCAGGCAAGTGCCCTT
AGAAACCGGGCCCCGCCCCCTTCCTGGCCTGCATTCCCATCCCCTCTCCCGGGGCGGAGGTGAGGACCT
CCTTGGTTCCTTTGGTTCTGTCAGTGAGCCCCTTCCTTGGCCATGAAGCTCGTGAGGAAGAACATCGAG
AAGGACAATGCGGGCCAGGTGACCCTGGTCCCCGAGGAGCCTGAGGACATGTGGCACACTTACAACCTC
GTGCAGGTGGGCGACAGCCTGCGCGCCTCCACCATCCGCAAGGTACAGACAGAGTCCTCCACGGGCAGC
GTGGGCAGCAACCGGGTCCGCACTACCCTCACTCTCTGCGTGGAGGCCATCGACTTCGACTCTCAAGCC
TGCCAGCTGCGGGTTAAGGGGACCAACATCCAAGAGAATGAGTATGTCAAGATGGGGGCTTACCACACC
ATCGAGCTGGAGCCCAACCGCCAGTTCACCCTGGCCAAGAAGCAGTGGGATAGTGTGGTACTGGAGCGC
ATCGAGCAGGCCTGTGACCCAGCCTGGAGCGCTGATGTGGCGGCTGTGGTCATGCAGGAAGGCCTCGCC
CATATCTGCTTAGTCACTCCCAGCATGACCCTCACTCGGGCCAAGGTGGAGGTGAACATCCCTAGGAAA
AGGAAAGGCAATTGCTCTCAGCATGACCGGGCCTTGGAGCGGTTCTATGAACAGGTGGTCCAGGCTATC
CAGCGCCACATACACTTTGATGTTGTAAAGTGCATCCTGGTGGCCAGCCCAGGATTTGTGAGGGAGCAG
TTCTGCGACTACATGTTTCAACAAGCAGTGAAGACCGACAACAAACTGCTCCTGGAAAACCGGTCCAAA
TTTCTTCAGGTACATGCCTCCTCCGGACACAAGTACTCCCTGAAAGAGGCCCTTTGTGACCCTACTGTG
GCTAGCCGCCTTTCAGACACTAAAGCTGCTGGGGAAGTCAAAGCCTTGGATGACTTCTATAAAATGTTA
CAGCATGAACCGGATCGAGCTTTCTATGGACTCAAGCAGGTGGAGAAGGCCAATGAAGCCATGGCAATT
GACACATTGCTCATCAGCGATGAGCTCTTCAGGCATCAGGATGTAGCCACACGGAGCCGGTATGTGAGG
CTGGTGGACAGTGTGAAAGAGAATGCAGGCACCGCTAGGATATTCTCTAGTCTTCACGTTTCTGGGGAA
CAGCTCAGCCAGTTGACTGGGGTAGCTGCCATTCTCCGCTTCCCTGTTCCCGAACTTTCTGACCAAGAG
GGTGATTCCAGTTCTGAAGAGGATTAATGATTGAAACTTAAAATTGAGACAATCTTGTGTTTCCTAAAC
TGTTACAGTACATTTCTCAGCATCCTTGTGACAGAAAGCTGCAAGAAGGGCACTTTTTGATTCATACAG
GGATTTCTTATGTCTTTGGCTACACTAGATATTTTGTGATTGGCAAGACATGTATTTAAACAATAAACT
AAAAGGAAATAATCTCCACGTACTACCAAAAAAAAAAAAAAAAAA.
```
[a] A nucleotide sequence of a human 68772. SEQ ID NO: 1.

TABLE 2[b]

MKLVRKNIEKDNAGQVTLVPEEPEDMWHTYNLVQVGDSLRASTIRKVQTESSTGSVGSNRVRTTLTLCV

EAIDFDSQACQLRVKGTNIQENEYVKMGAYHTIELEPNRQFTLAKKQWDSVVLERIEQACDPAWSADVA

AVVMQEGLAHICLVTPSMTLTRAKVEVNIPRKRKGNCSQHDRALERFYEQVVQAIQRHIHFDVVKCILV

ASPGFVREQFCDYMFQQAVKTDNKLLLENRSKFLQVHASSGHKYSLKEALCDPTVASRLSDTKAAGEVK

ALDDFYKMLQHEPDRAFYGLKQVEKANEAMAIDTLLISDELFRHQDVATRSRYVRLVDSVKENAGTARI

FSSLHVSGEQLSQLTGVAAILRFPVPELSDQEGDSSSEED.

[b]An amino acid of sequence of a human 68772. SEQ ID NO: 2.

One polynucleotide of the present invention encoding 68772 may be obtained using standard cloning and screening, from a cDNA library derived from mRNA in cells of human activated T-Cells, pancreas tumor, colon carcinoma, placenta, chondrosarcoma, hypoxic synoviocytes, osteoclastoma, tonsils, promyelocyte, heart, stimulated endothelial cells, and breast lymph node cells using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding 68772 polypeptide of SEQ ID NO:2 may be identical to the polypeptide encoding sequence contained in Table 1 (nucleotide number 250 to 1407 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of 68772 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding 68772 variants comprise the amino acid sequence 68772 polypeptide of Table 2 (SEQ ID NO:2) in which several, 5–10, 1–5, 1–3, 1–2 or 1 amino acid residues are substituted, deleted or added, in any combination.

The present invention further relates to polynuclcotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, or to the cDNA insert in the plasmid deposited at the ATCC with Deposit Number ATCC 98438 or a fragment thereof, may be used as hybridization probes for cDNA and genomic DNA, to isolate full-length cDNAs and genomic clones encoding 68772 polypeptide and to isolate cDNA and genomic clones of other genes that have a high sequence similarity to the 68772 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding 68772 polypeptide comprises the steps of screening an appropriate library under stingent hybridization conditions with a labeled probe having the SEQ ID NO: 1 or a fragment thereof, and isolating full-length cDNA and genomic clones containing said polynucleotide sequence. Thus in another aspect, 68772 polynucleotides of the present invention further include a nucleotide sequence comprising a nucleotide sequence that hybridize under stringent condition to a nucleotide sequence having SEQ ID NO: 1 or a fragment thereof Also included with 68772 polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the 68772 polypeptide is to be expressed for use in screening assays, generally, it is preferred that the polypeptide be produced at the surface of the cell. In this event, the cells may be harvested prior to use in the screening assay. If 68772 polypeptide is secreted into the medium, the medium can be recovered in order to recover and purify the polypeptide; if produced intracellularly, the cells must first be lysed before the polypeptide is recovered. 68772 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of 68772 polynucleotides for use as diagnostic reagents. Detection of a mutated form of 68772 gene associated with a dysfunction will provide a diagnostic tool that can add to or define a diagnosis of a disease or susceptibility to a disease which results from under-expression, over-expression or altered expression of 68772. Individuals carrying mutations in the 68772 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled 68772 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85: 4397–4401. In another embodiment, an array of oligonucleotides probes comprising 68772 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas through detection of mutation in the 68772 gene by the methods described.

In addition, proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, can be diagnosed by methods comprising determining from a sample derived from a subject an abnormally decreased or increased level of 68772 polypeptide or 68772 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an 68772 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly proliferative diseases such as leukemias, solid tumor cancers and metastases; chronic inflammatory proliferative diseases such as psoriasis and rheumatoid arthritis;

proliferative cardiovascular diseases such as restenosis; prolifertive ocular disorders such as diabetic retinopathy; and benign hyperproliferative diseases such as hemangiomas, which comprises:

(a) a 68772 polynucleotide, preferably the nucleotide sequence of SEQ ID NO: 1, or a fragment thereof;

(b) a nucleotide sequence complementary to that of (a);

(c) a 68772 polypeptide, preferably the polypeptide of SEQ ID NO: 2, or a fragment thereof; or (d) an antibody to a 68772 polypeptide, preferably to the polypeptide of SEQ ID NO: 2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the 68772 polypeptides. The term "immunospecific" means that the antibodies have substantiall greater affinity for the polypeptides of the invention than their affinity for other related polypeptides in the prior art.

Antibodies generated against the 68772 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against 68772 polypeptides may also be employed to treat proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, among others.

Vaccines

Another aspect of the invention relates to a method for inducing an immunological response in a mammal which comprises inoculating the mammal with 68772 polypeptide, or a fragment thereof, adequate to produce antibody and/or T cell immune response to protect said animal from proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, among others. Yet another aspect of the invention relates to a method of inducing immunological response in a mammal which comprises, delivering 68772 polypeptide via a vector directing expression of 68772 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a 68772 polypeptide wherein the composition comprises a 68772 polypeptide or 68772 gene. The vaccine formulation may further comprise a suitable carrier. Since 68772 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The 68772 polypeptide of the present invention may be employed in a screening process for compounds which activate (agonists) or inhibit activation of (antagonists, or otherwise called inhibitors) the 68772 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., *Current Protocols in Immunology* 1(2):Chapter 5 (1991).

68772 polypeptides are responsible for many biological functions, including many pathologies. Accordingly, it is desirous to find compounds and drugs which stimulate 68772 polypeptide on the one hand and which can inhibit the function of 68772 polypeptide on the other hand. In general, agonists are employed for therapeutic and prophylactic purposes for such conditions as proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas. Antagonists may be employed for a variety of therapeutic and prophylactic purposes for such conditions as proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas.

In general, such screening procedures may involve using appropriate cells which express the 68772 polypeptide or respond to 68772 polypeptide of the present invention. Such cells include cells from mammals, yeast, Drosophila or *E. coli*. Cells which express the 68772 polypeptide (or cell membrane containing the expressed polypeptide) or respond to 68772 polypeptide are then contacted with a test compound to observe binding, or stimulation or inhibition of a functional response. The ability of the cells which were contacted with the candidate compounds is compared with the same cells which were not contacted for 68772 activity.

The assays may simply test binding of a candidate compound wherein adherence to the cells bearing the 68772 polypeptide is detected by means of a label directly or indirectly associated with the candidate compound or in an assay involving competition with a labeled competitor. Further, these assays may test whether the candidate compound results in a signal generated by activation of the 68772 polypeptide, using detection systems appropriate to the cells bearing the 68772 polypeptide. Inhibitors of activation are generally assayed in the presence of a known agonist and the effect on activation by the agonist by the presence of the candidate compound is observed.

The 68772 cDNA, protein and antibodies to the protein may also be used to configure assays for detecting the effect of added compounds on the production of 68772 mRNA and protein in cells. For example, an ELISA may be constructed for measuring secreted or cell associated levels of 68772 protein using monoclonal and polyclonal antibodies by standard methods known in the art, and this can be used to discover agents which may inhibit or enhance the production of 68772 (also called antagonist or agonist, respectively) from suitably manipulated cells or tissues. Standard methods for conducting screening assays are well understood in the art.

The 68772 protein may be used to identify membrane bound or soluble receptors, if any, through standard receptor binding techniques known in the art. These include, but are not limited to, ligand binding and crosslinking assays in which the 68772 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of 68772 which compete with the binding of 68772 to its receptors, if any. Standard methods for conducting screening assays are well understood in the art.

Examples of potential 68772 polypeptide antagonists include antibodies or, in some cases, oligonucleotides or proteins which are closely related to the ligands, substrates, receptors, enzymes, etc., as the case may be, of the 68772 polypeptide, e.g., a fragment of the ligands, substrates, receptors, enzymes, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for 68772 polypeptides; or compounds which decrease or enhance the production of 68772 polypeptides, which comprises:

(a) a 68772 polypeptide, preferably that of SEQ ID NO:2;

(b) a recombinant cell expressing a 68772 polypeptide, preferably that of SEQ ID NO:2;

(c) a cell membrane expressing a 68772 polypeptide; preferably that of SEQ ID NO: 2; or (d) antibody to a 68772 polypeptide, preferably that of SEQ ID NO: 2. It will be appreciated that in any such kit, (a), (b), (c) or (d) may comprise a substantial component.

Prophylactic and Therapeutic Methods

This invention provides methods of treating abnormal conditions such as, proliferative diseases such as leukemias, solid tumor cancers and metastases; chronic inflammatory proliferative diseases such as psoriasis and rheumatoid arthritis; proliferative cardiovascular diseases such as restenosis; prolifertive ocular disorders such as diabetic retinopathy; and benign hyperproliferative diseases such as hemangiomas, related to both an excess of and insufficient amounts of 68772 polypeptide activity.

If the activity of 68772 polypeptide is in excess, several approaches are available. One approach comprises administering to a subject an inhibitor compound (antagonist) as hereinabove described along with a pharmaceutically acceptable carrier in an amount effective to inhibit the function of the 68772 polypeptide, such as, for example, by blocking the binding of ligands, substrates, enzymes, receptors, etc., or by inhibiting a second signal, and thereby alleviating the abnormal condition. In another approach, soluble forms of 68772 polypeptides still capable of binding the ligand, substrate, enzymes, receptors, etc. in competition with endogenous 68772 polypeptide may be administered. Typical embodiments of such competitors comprise fragments of the 68772 polypeptide.

In still another approach, expression of the gene encoding endogenous 68772 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of 68772 and its activity, several approaches are also available. One approach comprises administering to a subject a therapeutically effective amount of a compound which activates 68772 polypeptide, i.e., an agonist as described above, in combination with a pharmaceutically acceptable carrier, to thereby alleviate the abnormal condition. Alternatively, gene therapy may be employed to effect the endogenous production of 68772 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer therapeutic amount of 68772 polypeptides in combination with a suitable pharmaceutical carrier.

Formulation and Administration

Peptides, such as the soluble form of 68772 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

The full-length clone (68772) was identified through searches of the Human Genome Sciences database.

Northern blotting of multiple tissue human RNA blots performed using 68772 (human pelota) as a probe, detected a message of approximately 1.9 kb in several cancer cell lines: HL-60, HelaS3, K-562, MOLT-4, Raji, SW480, A549, and G361. The message was also found in fetal liver, peripheral blood lymphocytes, and also weakly expressed in bone marrow and thymus. No apparent message was detected in brain, spleen, appendix, lymph node, heart, placenta, lung, liver, skeletal muscle, kidney, or pancreas.

All publications, including but not limited to patents and patent applications, cited in this specification are herein incorporated by reference as if each individual publication were specifically and individually indicated to be incorporated by reference herein as though fully set forth.

What is claimed is:

1. A process for producing a 68772 polypeptide comprising culturing a host of a cell comprised of an expression system which is capable of producing a 68772 polypeptide under conditions sufficient for the production of said polypeptide and recovering the polypeptide from the culture.

2. A process for producing a cell which produces a 68772 polypeptide thereof comprising transforming or transfecting a host cell with an expression system capable of producing the 68772 polypeptide such that the host cell, under appropriate culture conditions, produces a 68772 polypeptide.

* * * * *